United States Patent
Singh

(10) Patent No.: US 9,610,102 B2
(45) Date of Patent: Apr. 4, 2017

(54) BONE POSITION TRACKING SYSTEM

(71) Applicant: Stryker Trauma GmbH, Schönkirchen (DE)

(72) Inventor: Manoj Kumar Singh, Mahwah, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 321 days.

(21) Appl. No.: 14/038,004

(22) Filed: Sep. 26, 2013

(65) Prior Publication Data

US 2015/0088135 A1 Mar. 26, 2015

(51) Int. Cl.
*A61B 17/62* (2006.01)
*A61B 17/66* (2006.01)
*A61B 34/20* (2016.01)

(52) U.S. Cl.
CPC .............. *A61B 17/62* (2013.01); *A61B 17/66* (2013.01); *A61B 2034/2051* (2016.02)

(58) Field of Classification Search
CPC ........ A61B 17/62; A61B 17/645; A61B 17/66
See application file for complete search history.

(56) References Cited

U.S. PATENT DOCUMENTS

| | | | |
|---|---|---|---|
| 5,880,976 A | 3/1999 | DiGioia, III et al. | |
| 6,030,386 A | 2/2000 | Taylor et al. | |
| 6,701,174 B1 | 3/2004 | Krause et al. | |
| 7,837,621 B2 | 11/2010 | Krause et al. | |
| 8,333,766 B2 | 12/2012 | Edelhauser et al. | |
| 2002/0010465 A1 | 1/2002 | Koo et al. | |
| 2005/0020909 A1* | 1/2005 | Moctezuma de la Barrera | A61B 34/20 600/424 |
| 2008/0004633 A1* | 1/2008 | Arata | A61B 19/5244 606/130 |
| 2011/0313418 A1* | 12/2011 | Nikonovas | A61B 17/62 606/56 |

OTHER PUBLICATIONS

U.S. Appl. No. 13/592,832.

* cited by examiner

*Primary Examiner* — Eduardo C Robert
*Assistant Examiner* — Julianna N Harvey
(74) *Attorney, Agent, or Firm* — Lerner, David, Littenberg, Krumholz & Mentlik, LLP

(57) ABSTRACT

A method of correcting a bone deformity includes fixing first and second support members to first and second fragments of a bone, respectively. The first support member may have a receiver connected thereto. First and second tracking devices are connected to the first and second bone fragments, respectively. A deformity correction plan is determined, and a position of the first support member is adjusted relative to the second support member based on the plan. Location data is transmitted from the first and second trackers to the receiver. Based on the tracker location data, a real position of the first and second bone fragments is determined. The real position of the first and second bone fragment is compared to the deformity correction plan, and the deformity correction plan is reprogrammed based on the comparison. The first and second support members may then be adjusted based on the reprogrammed deformity correction plan.

9 Claims, 4 Drawing Sheets

600

BONE POSITION TRACKING SYSTEM

FIELD OF THE INVENTION

The present invention relates to systems and methods for tracking the position and orientation of a plurality of bone fragments with respect to one another, and in particular it relates to a tracking system for use with an external fixation device attached to a plurality of bone segments.

BACKGROUND OF THE INVENTION

External fixation frames may be used to correct skeletal deformities. The Ilizarov external fixation devices, for example, are widely used for this purpose. The Ilizarov-type devices may be used to translate bone segments by manipulating rings connected to each bone segment and a plurality of threaded rods connected to the manipulation rings.

A bone fragment can be moved, in general, from its original position as in a nonunion or malunion or from its intended position as in congenital deformities along six separate axes, a combination of three orthogonal translational axes (e.g., typical "X," "Y" and "Z" axes) and three orthogonal rotational axes (e.g., rotation about such typical "X," "Y" and "Z" axes). This movement generally occurs via manipulation of one or more adjustable length struts connected at each end thereof to rings of the external fixation device.

External fixation devices are generally attached to the boney skeleton, such as the femur or tibia, for example, with threaded and/or smooth pins and/or threaded and/or smooth and/or beaded wires. Such constructs are commonly referred to as orthopedic external fixators or external skeletal fixators. External fixators may be utilized to treat acute fractures of the skeleton, soft tissue injuries, delayed union of the skeleton when bones are slow to heal, nonunion of the skeleton when bones have not healed, malunion whereby broken or fractures bones have healed in a malposition, congenital deformities whereby bones develop a malposition, and bone lengthening, widening, or twisting.

Examples of external fixation devices include those described in U.S. Pat. No. 8,333,766 and U.S. patent application Ser. No. 13/592,832, the entire disclosures of both of which are hereby incorporated by reference herein. After a bone is fixed to such an external fixation device, one bone fragment may be moved in any combination of the six degrees of freedom relative to a fixed bone fragment. The movement is generally directed by a preoperative and/or postoperative plan defining precise movement of rings and/or struts to result in precise movement of one bone fragment relative to a fixed bone fragment. Despite following instructions provided by the plan, the deformity correction may not occur according to plan for a variety of reasons. Such errors between planned movements of the bone fragment relative to the fixed bone fragment may occur, for example, because of incorrect adjustments to the external fixation device or bending and other deformation of wires, pins, or other devices connecting the bone fragments to the external fixation device. Errors may also result from imprecision in, or deformation of, other components of the external fixation device, or from human error in following the deformity correction plan.

One way of determining whether planned movements are occurring correctly are markings on the struts themselves which may include numbers on an outside body of a strut indicating the length of the strut measured between ends thereof. As a particular strut is compressed or expanded, the change in length of the strut can be visualized via the markings. Such marking are found on adjustable length struts as shown, for example, in U.S. Pat. No. 6,030,386. In other devices, the change in length of struts is digitally displayed on the struts themselves such as shown in U.S. Pat. Pub. No. 2002/0010465. However, not only is it difficult to correlate the change in length of a strut and the position and orientation of respective bone fragments, this relationship is not always accurate based on the aforementioned deformation of wires, pins, or other devices connecting the bone fragments to the external fixation device. There is need for a device or method for tracking the movements of bone fragment relative to one another to determine if such movements are occurring accurately according to a deformity correction plan.

BRIEF SUMMARY OF THE INVENTION

The present invention is directed to apparatus and methods for tracking the position of bone fragments during a deformity correction, and using the position data to modify the original deformity correction plan to correct for errors in the real bone position compared to the deformity correction plan.

In one embodiment an external fixation system includes a first support member connected to a first bone fragment and a second support member connected to a second bone fragment. A plurality of struts may connect the first support member to the second support member, and a first tracking device may be connected to one of the first and second bone fragments. The first tracking device may be configured to transmit tracker location data corresponding to a location of the one of the first and second bone fragments to which the first tracking device is connected. The system may also include a second tracking device connected to the other of the first and second bone fragments, and may also include a receiver in communication with the first and second tracking devices, wherein the first and second tracking devices are configured to transmit tracker location data to the receiver. The first and second tracking devices may each be wirelessly connected to the receiver, and the receiver may include a processor configured to determine the location of the first and second bone fragments based on the tracker location data. The tracker location data may correspond to real positions of the first and second bone fragments. The first and second support members may each comprise plate type supports, for example those selected from the group consisting of full rings, half-rings, and u-shaped rings.

In another embodiment, an external fixation system includes a first support member and a first tracking device connected to a first bone fragment, and a second tracking device connected to a second bone fragment. A receiver may be in communication with the first and second tracking devices, wherein the first and second tracking devices are configured to transmit tracker location data to the receiver, the tracker location data corresponding to three-dimensional coordinate data points of a location of the first and second tracking devices connected to the first and second bone fragments. The system may also include a second support member connected to the second bone fragment. The first and second support members may each comprise plate type supports, for example those selected from the group consisting of full rings, half-rings, and u-shaped rings. The first support member may be connected to the second support member by a plurality of struts. The first and second tracking devices may each be wirelessly connected to the receiver. The receiver may include a processor configured to determine the location of the first and second bone fragments based on the tracker location data.

In a further embodiment, a method of correcting a bone deformity includes the steps of fixing a first support member to a bone fragment and fixing a second support member to a second bone fragment. The method may also include fixing first and second tracking devices to the first and second bone fragments, respectively. The method may include determining a deformity correction plan, and adjusting a position of the first support member relative to the second support member based on the deformity correction plan. Location data may be transmitted from the first and second trackers to a receiver. The method may also include the step of determining, based on the tracker location data, a real position of the first and second bone fragments. The receiver may be connected to the first support member.

The method may also include comparing the real position of the first and second bone fragments to the deformity correction plan and reprogramming the deformity correction plan based on the comparison. The method may further include adjusting the position of the first support member relative to the second support member based on the reprogrammed deformity correction plan. The steps of fixing the first and second tracking devices to the respective first and second bone fragments may include inserting pins of the first and second tracking devices into the respective first and second bone fragments.

DETAILED DESCRIPTION

As used herein, the term "distal" means more distant from the heart and the term "proximal" means closer to the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Figure 1:
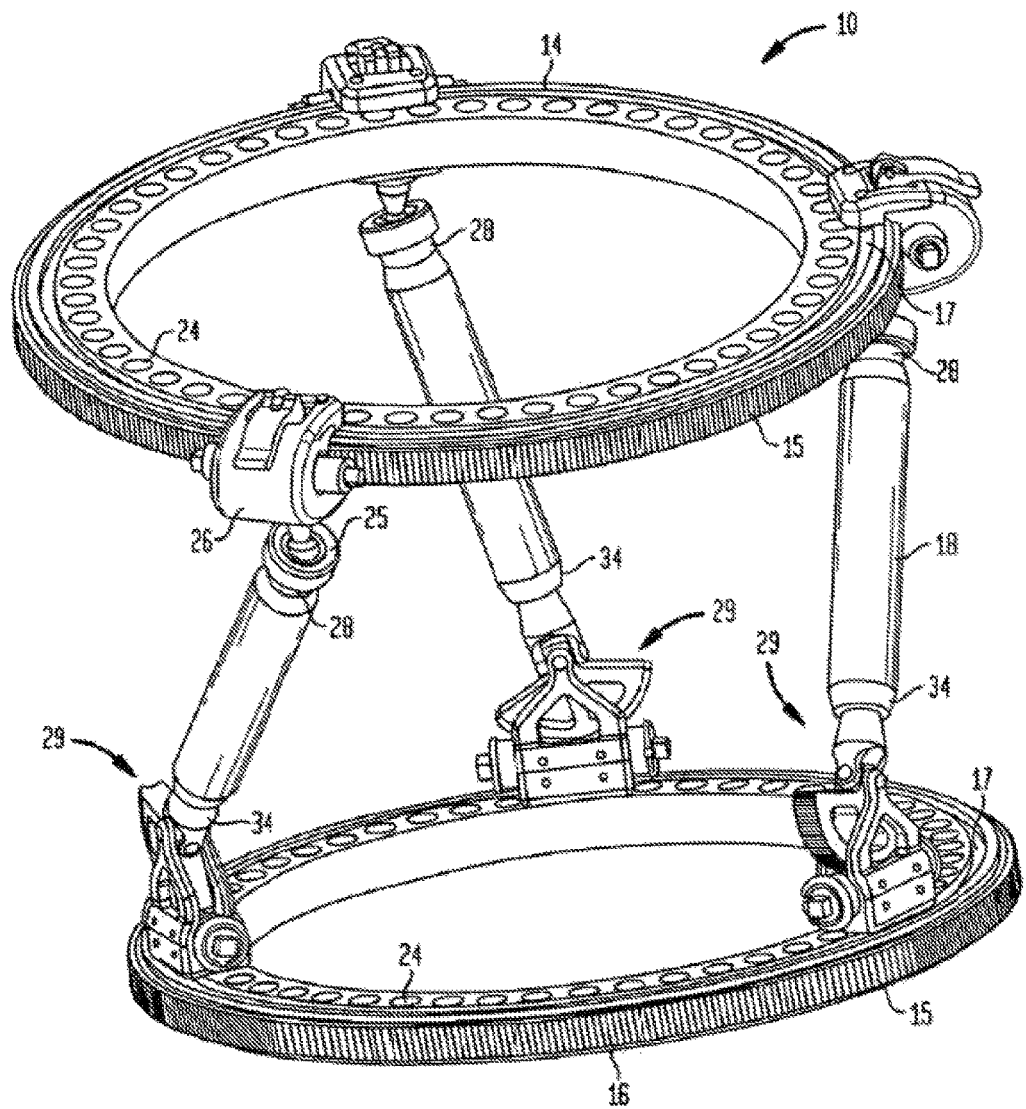
FIG. 1 is a perspective view of an external fixation device according to the prior art.

Referring to FIG. 1, there is shown the external fixation system 10 for correcting a bone deformity according to the prior art. The external fixation system 10 may be utilized with any long bone, in particular, the tibia and the femur.

As shown in FIG. 1, the external fixation system 10 includes a first ring 14 and a second ring 16. In some embodiments, both rings 14, 16 are identical. Each ring 14 includes a worm gear 15 formed around its outer circumference. Two grooves 17 are formed in the upper and lower surfaces of ring 14 around its circumference adjacent the worm gear 15. Ring 14 (or 16) may include a multi level configuration with the upper and lower surfaces having alternate steps including through holes 24. Such an external fixation ring (without the circumferential worm gear) is described in U.S. Pat. No. 7,955,334, the entire disclosure of which is incorporated herein by reference. In certain embodiments, rings 14, 16 are connected by three variable length struts 18. The three struts 18 have first ends 28 mounted to the first ring 14 via a connector 25 coupled to a sliding or shuttle unit 26, which is circumferentially moveable around ring 14. In several embodiments, the first ends 28 are connected to sliding units or connector 26 by a connector 25 having a ball or spherical joint. As is typical, the rings are connected to a tibia (not illustrated in FIG. 1) by a plurality of bone pins or wires (not shown). In some embodiments, the pins or wires are connected to each ring 14, 16 by connection elements, which are located in one or more of a multiplicity of holes 24 around the circumference of the first and second rings 14 and 16. Although holes 24 are shown, any structure which locates the pins or wires with respect to the circumference of rings 14 and 16 can be utilized. Lower ends 34 of struts 18 may be connected to lower ring 16 by standard universal-joints, which allow free rotation about only two axes rather than the three axes of the spherical joint at the first strut end 28.

Ring 14 may be coupled to a first bone element via pins or wires and, similarly, ring 16 is coupled to a second bone element by similar pins or wires. Shuttle unit 26 is slidable about ring 14 in a track and is preferably driven by a servo motor. A second connector 29 between strut 18 and second lower ring 16 has a standard universal joint, which allows the strut to rotate freely about two axes oriented perpendicular with respect to the one another. The universal joint may also be powered by servo motors. Thus, each of the three sliding shuttle units 26 may be independently controlled and the three connectors 29 at the second ring 16 may be independently controlled so that the ring 14, and therefore the bone element attached to ring 14, can be positioned in proper alignment with ring 16 and the bone element attached to ring 16. Rings 14 and 16 can be repositioned after their initial alignment as desired by the surgeon. In addition, the movement can be programmed into a computer means, which can automatically increment movement, for example, on a daily basis. Strut 18 is of variable length but can be locked at a desired length after the surgeon initially sets the starting location of the system.

Figure 2:
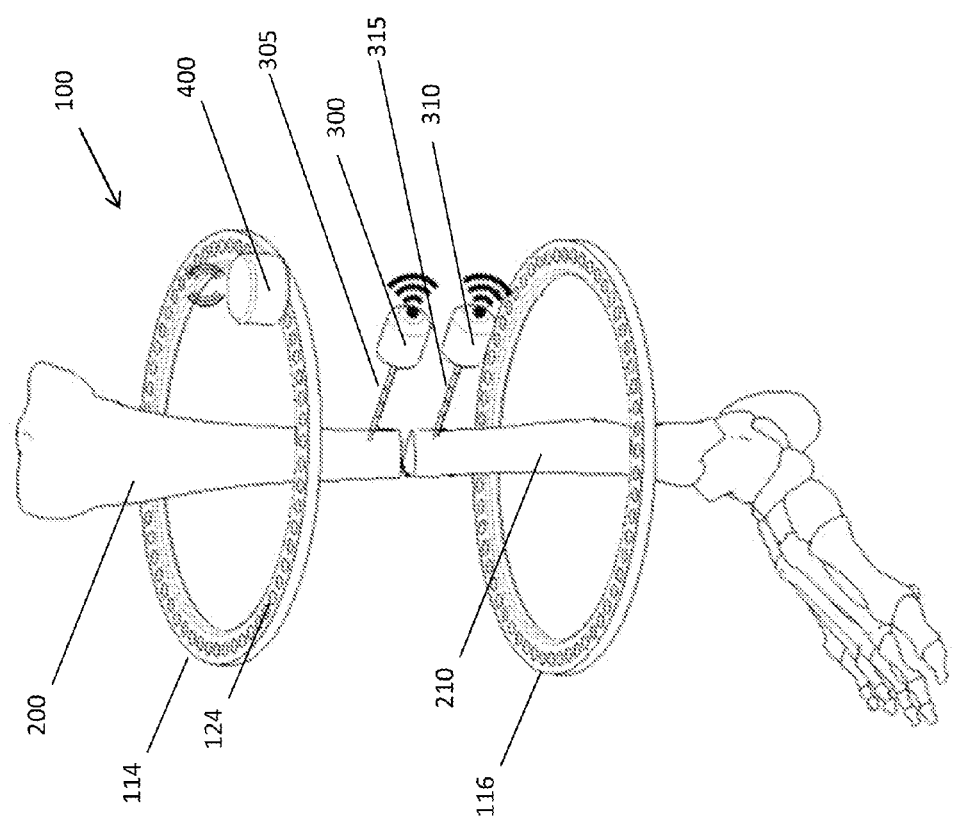
FIG. 2 is a perspective view of an external fixation device with tracking devices positioned on a bone according to an aspect of the invention.
Figure 3:
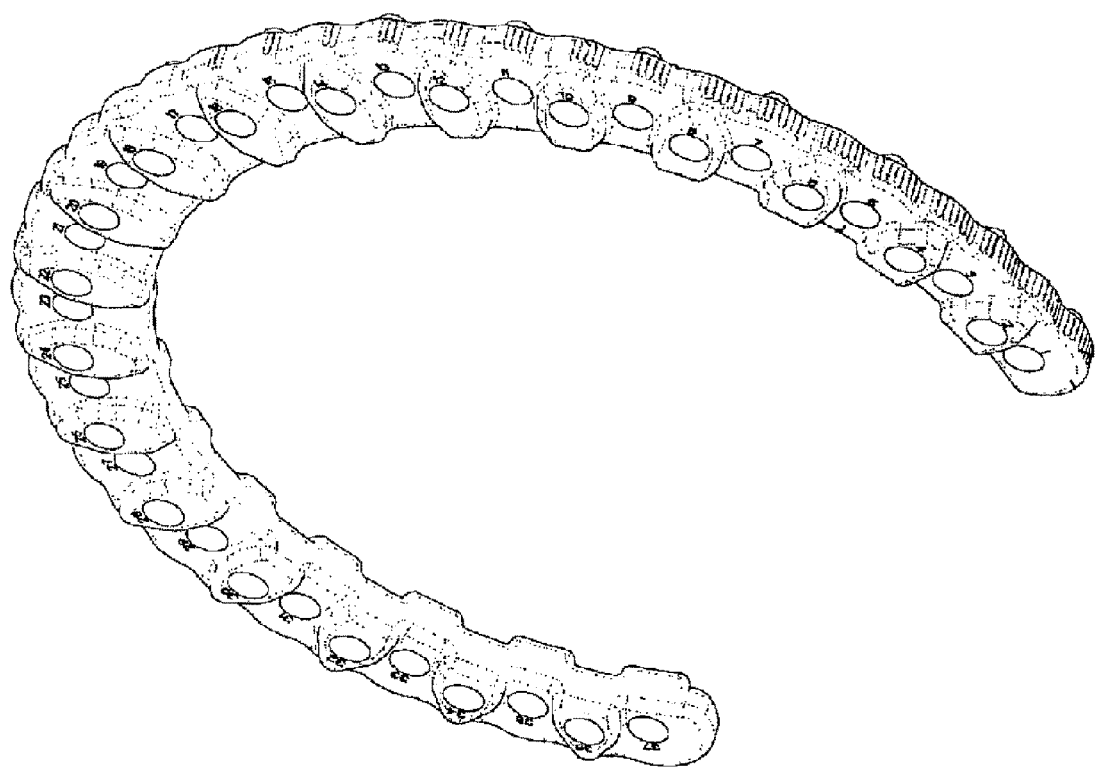
FIG. 3 is a perspective view of an example of a half ring.
Figure 4:
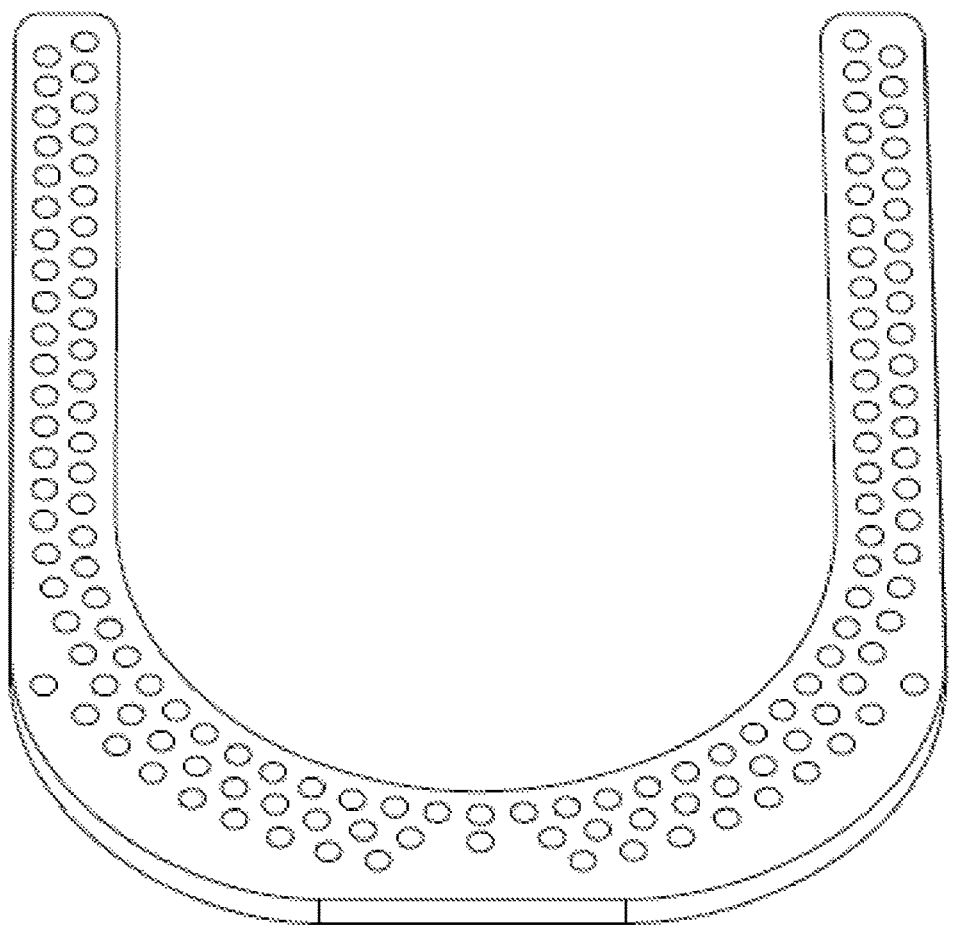
FIG. 4 is a top view of an example of a U-shaped ring.

Referring to FIG. 2, there are shown portions of an external fixation system 100 according to an aspect of the invention. Generally, the external fixation system 100 includes a first support member, such as a first ring 114, and a second support member, such as a second ring 116. Although the connections between first and second ring 114, 116 are not illustrated in FIG. 2, the connections may be similar or identical to those described with respect to FIG. 1 or may take the form of other connections known in the art. For example, the first support member 114 may be connected to the second support member 116 by a plurality of struts. It should also be understood that, although support members 114, 116 take the form of full rings in FIG. 2, other support members, including plate type supports other than rings, are suitable for use in the present invention, such as half rings 500 (FIG. 3) or u-shaped rings 600 (FIG. 4), for example.

The first ring 114 is attached to a first bone fragment, illustrated as a proximal portion of a tibia 200, and the second ring 116 is attached to a second bone fragment, illustrated as a distal portion of a tibia 210. For purposes of this disclosure, proximal portion 200 is also referred to as the "fixed fragment," and distal portion 200 is also referred to as the "moving fragment." It should be understood, however, that proximal portion 200 and distal portion 210 move relative to one another, and the use of the terms "moving fragment" and "fixed fragment" are used only as a convention for convenience. The first and second ring 114, 116 may be attached to the first and second bone fragments 200, 210 by conventional means, including wires and/or pins (not shown).

The external fixation system 100 further includes a first tracking device 300 fixed to the fixed fragment 200 and a second tracking device 310 fixed to the moving fragment 210. The first and second tracking devices 300, 310 may be fixed to the fixed and moving fragments 200, 210 by bone pins 305, 315, respectively. Tracking devices known in the art may be suitable for the use disclosed herein, such as the Aurora® Electromagnetic Tracking System, available from Northern Digital, Inc. of Ontario, Canada. This example is merely illustrative, and other tracking devices may also be suitable for the use disclosed herein. Preferably, the first and second tracking devices 300, 310, including bone pins 305, 315, are placed along the same plane, although any relative positioning is suitable. It should be understood that other types of connectors or fasteners besides bone pins 305, 315 may also be suitable for connecting the tracking devices 200, 210 to the bone fragments 300, 310.

The external fixation system 100 also includes a receiver 400. The receiver 400 may be fixed to the first or second ring 114, 116, but is preferably fixed to the first ring along with the fixed fragment 200. The receiver 400 may be attached, for example, to a through-hole 124 of the first ring 114, although other suitable means for attachment may be used. It should also be understood that receiver 400 need not be directly attached to external fixation system 100, but may, for example, be located nearby in range of communication with first and second tracking devices 300, 310.

The tracking devices 200, 210 preferably each communicate with the receiver 400 wirelessly, although the communication may be wired. As the deformity correction procedure takes place, with the moving fragment 210 changing position with respect to the fixed fragment 200, the second tracking device 310 will move relative to the first tracking device 300. The tracking devices 300, 310 are each configured to transmit position/location data to the receiver 400. The relative change in positions of the tracking devices 300, 310, including the change in three orthogonal translational (X, Y, Z) axes and three orthogonal rotational axes (rotation about the X, Y, Z axes) may be determined based on the position/location data. This data is preferably acquired using a real-time locating system ("RTLS") or global positioning system ("GPS"), but other methods may be suitable. The format of the tracker location data may be, for example, three-dimensional coordinate data points of a location of a point on the respective tracking device. Other formats may also be suitable. For example, multiple points on a tracking device may be registered and tracked to better represent changes in the real position of the bone fragment to which the tracking device is connected. Based on the information regarding change in the relative positions of the tracking devices 300, 310 and based on the initial relative positions of the tracking devices, the position of the moving fragment 210 with respect to the fixed fragment 200 may be calculated. Such a calculation may take place in a processor in the receiver 400, with the receiver also functioning as a transmitter and transmitting data to another device such as a personal computer which may further process the data. Alternatively, the data from the tracking devices 300, 310 may be transmitted to the receiver 400, which may then transmit the data to another device, such as a computer, that will perform calculations of the relative positions of the bone fragments 200, 210. In addition or alternatively to the relative positions of the fixed and moving fragment 200, 210, the data may be used to calculate a bone correction curve, which may in turn be used calculate the real position of the bone fragments for comparison to the deformity correction plan.

Once the relative positions of the bone fragments 200, 210, and/or the bone correction curve are determined, the current positions and/or bone correction curve may be compared to planned deformity correction to determine, for example, if the deformity correction is proceeding as planned. If the deformity correction is not proceeding as planned, the deformity correction plan may be reprogrammed to achieve the desired deformity correction. The position data is preferably transmitted on a real time continuous basis, but such data transmission may be periodic. If the deformity correction plan is reprogrammed, the new plan may be provided directly to the patient wirelessly by SMS, email and/or uploading the new data to automatic position adjusting tools. An automatic position adjusting tool, such as that described in U.S. Patent Publication No. 2012/0150180 the entire contents of which are hereby incorporated by reference herein, may be used by the patient to automatically adjust components of the external fixation system 100 to position the bone fragments 200, 210 according to an updated deformity correction plan. Also the data may additionally be transmitted, for example by satellite or SMS, to a surgeon or other medical personnel for further consideration.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:
1. An external fixation system for achieving a desired deformity correction, the system comprising:
a first support member configured to connect to a first bone fragment;
a second support member configured to connect to a second bone fragment;
a plurality of struts connecting the first support member to the second support member;
a first tracking device configured to directly connect to the first bone fragment in a first plane and to transmit tracker location data to a receiver corresponding to a location of the first bone fragment; and
a second tracking device configured to directly connect to the second bone fragment in the first plane and to transmit tracker location data to the receiver corresponding to a location of the second bone fragment;
wherein the receiver is configured to determine a position of the first bone fragment relative to the second bone fragment based on a relative change in positions of the first and second tracking devices, including the change in three orthogonal translational axes and three orthogonal rotational axes to determine a current deformity correction, and is further configured to compare the current deformity correction to a planned deformity correction to determine if the current deformity correction is proceeding according to the planned deformity correction.

2. The external fixation system of claim 1, wherein the first and second tracking devices are each wirelessly connected to the receiver.

3. The external fixation system of claim 2, wherein the receiver includes a processor configured to determine the location of the first and second bone fragments based on the tracker location data.

4. The external fixation system of claim 1, wherein the tracker location data corresponds to real positions of the first and second bone fragments.

5. The external fixation system of claim 1, wherein the first and second support members each comprise plate type supports.

6. The external fixation system of claim 5, wherein the plate type supports are each selected from the group consisting of full rings, half-rings, and u-shaped rings.

7. The external fixation system of claim 1, wherein the first tracking device includes a bone pin.

8. The external fixation system of claim 1, wherein the receiver is directly coupled to the first or second support member.

9. The external fixation system of claim 1, wherein the receiver is further configured to reprogram the planned deformity correction to achieve the desired deformity correction if the current deformity correction is not proceeding according to the planned deformity correction.

* * * * *